(12) United States Patent
Yagami et al.

(10) Patent No.: US 9,814,545 B2
(45) Date of Patent: Nov. 14, 2017

(54) IMPLANT STRUCTURE

(71) Applicants: MATSUMOTO DENTAL UNIVERSITY, Shiojiri-shi (JP); HI-LEX CORPORATION, Takarazuka-shi (JP)

(72) Inventors: Kimitoshi Yagami, Shiojiri (JP); Yasuo Seki, Takarazuka (JP); Kazutaka Yoshino, Takarazuka (JP)

(73) Assignees: MATSUMOTO DENTAL UNIVERSITY, Shiojiri-shi (JP); HI-LEX CORPORATION, Takarazuka-shi (JP)

( * ) Notice: Subject to any disclaimer, the term of this patent is extended or adjusted under 35 U.S.C. 154(b) by 0 days.

(21) Appl. No.: 14/351,708

(22) PCT Filed: Oct. 15, 2012

(86) PCT No.: PCT/JP2012/076622
§ 371 (c)(1),
(2) Date: Apr. 14, 2014

(87) PCT Pub. No.: WO2013/054935
PCT Pub. Date: Apr. 18, 2013

(65) Prior Publication Data
US 2014/0315151 A1    Oct. 23, 2014

(30) Foreign Application Priority Data
Oct. 13, 2011 (JP) .................. 2011-226008

(51) Int. Cl.
*A61C 11/00* (2006.01)
*A61C 8/00* (2006.01)
*A61C 13/08* (2006.01)

(52) U.S. Cl.
CPC ............. *A61C 8/0012* (2013.01); *A61C 8/005* (2013.01); *A61C 8/0022* (2013.01);
(Continued)

(58) Field of Classification Search
CPC ..... A61C 8/0048; A61C 8/005; A61C 8/0022; A61C 8/00; A61C 8/0037; A61C 8/0045;
(Continued)

(56) References Cited

U.S. PATENT DOCUMENTS 3,934,347 A * 1/1976 Lash et al. .................. 433/173
5,727,945 A * 3/1998 Dannenbaum ............... 433/215
(Continued)

FOREIGN PATENT DOCUMENTS

JP    S60-207659    10/1985
JP    2005-528183 A1    9/2005
(Continued)

OTHER PUBLICATIONS

International Search Report for International Application No. PCT/JP2012/076622 dated Dec. 25, 2012.
(Continued)

*Primary Examiner* — Yogesh Patel
(74) *Attorney, Agent, or Firm* — Kratz, Quintos & Hanson, LLP

(57) ABSTRACT

An object of the present invention is to provide an implant structure assuring that substances accelerating breeding of bacteria are hard to be induced. The implant structure comprises: an artificial tooth root including an artificial tooth root main body having a distal end portion and a proximal end portion and a thread being formed at least on the distal end portion side and an induction portion for inducing a soft tissue provided on an outer periphery of the proximal end portion of the artificial tooth root main body; and a support base having a covering portion at the proximal end portion
(Continued)

Figure 1A:
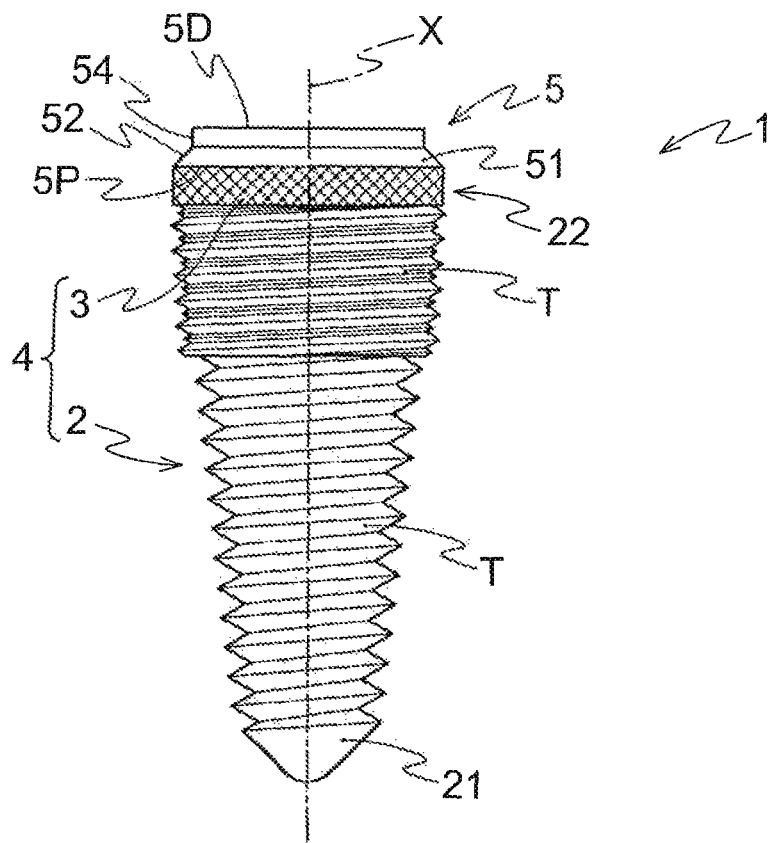

side of the support base covering the whole surface of the proximal end portion side of the induction portion, wherein the support base is provided with a step portion along its outer periphery from the covering portion toward a distal end side of the support base.

6 Claims, 5 Drawing Sheets

(52) U.S. Cl.
CPC .......... *A61C 8/0025* (2013.01); *A61C 8/0068* (2013.01); *A61C 13/08* (2013.01)

(58) Field of Classification Search
CPC ... A61C 8/0069; A61C 8/0071; A61C 8/0074; A61C 8/0075; A61C 2008/0046
USPC .................................................. 433/172–176
See application file for complete search history.

(56) References Cited

U.S. PATENT DOCUMENTS

| | | | | |
|---|---|---|---|---|
| 6,273,720 | B1* | 8/2001 | Spalten ................ | A61C 8/0009 433/172 |
| 2003/0124489 | A1* | 7/2003 | Hurson et al. ................ | 433/173 |
| 2004/0142304 | A1* | 7/2004 | Cottrell .......................... | 433/173 |
| 2007/0281280 | A1* | 12/2007 | Graham ............... | A61C 8/0075 433/174 |
| 2008/0020349 | A1* | 1/2008 | Dricot .................. | A61C 8/0012 433/174 |
| 2010/0003638 | A1 | 1/2010 | Collins | |
| 2011/0200969 | A1* | 8/2011 | Schroering .......... | A61C 8/0018 433/174 |

FOREIGN PATENT DOCUMENTS

| | | |
|---|---|---|
| JP | 2007-513680 A1 | 5/2007 |
| JP | 2010-279653 A1 | 12/2010 |
| JP | 2011-135932 A1 | 7/2011 |
| WO | WO 03/103527 A2 | 12/2003 |
| WO | WO 2005/055858 A1 | 6/2005 |
| WO | 2011/066098 A1 | 6/2011 |

OTHER PUBLICATIONS

Japanese Decision of Final Rejection in Patent Application No. 2011-226008 dated Jul. 26, 2016, and its English translation.

* cited by examiner

IMPLANT STRUCTURE

TECHNICAL FIELD

The present invention relates to an implant structure intended to inhibit bacteria and substances accelerating breeding thereof from directly reaching a joint portion between an implant and a gingiva/bone, and further intended to prevent and inhibit bone absorption at a periphery of upper portion of the implant.

BACKGROUND ART

Recently in a dental treatment, an implant treatment where an artificial tooth is attached to the artificial tooth root that is implanted in a jawbone instead of a lost tooth with an external thread on its outer periphery is prevailing. The artificial tooth root is implanted in the jawbone from which a tooth has been lost and is functional as a base for the artificial tooth to be attached to the tooth root. In an operation for implanting the artificial tooth root, the artificial tooth root is inserted into a hole of the jawbone formed in the same size as that of the artificial tooth root by screw-fitting, and the artificial tooth root is connected to the jawbone by forming a bone around the artificial tooth root. However, if the hole formed in the bone is larger than the artificial tooth root or the bone around the artificial tooth root is osteoporotic, there is a case where connection to the jawbone requires a long period of time or finally the artificial tooth root is not connected to the jawbone firmly.

Further, a connective tissue of a living body cannot be connected directly to the artificial tooth root, and therefore, there is nothing replacing a periodontal membrane and a periodontal ligament for supporting a tooth on the bone and the gingiva. Accordingly, various substances in a mouth enter into a space between the bone and the artificial tooth root, and bacterial infection and resultant inflammation of the gingiva and the bone arise continuously, thereby progressing bone absorption around the implant. As a result, an epithelium (gingiva) grows toward the bottom of the hole formed in the jawbone (down-growth), namely, the gingiva grows so as to intervene between the artificial tooth root and the jawbone, and there is no connection between the artificial tooth root and the jawbone. Furthermore, in the case of fixing the artificial tooth root to the jawbone using a thread, even if the artificial tooth root is fitted to the jawbone without a space therebetween, a fibrous tissue and an inflammatory tissue grow into the thread groove and a bone does not grow at the side of the upper portion of a thread, namely, no adhesion of the bone and the gingiva onto the upper portion of the thread is obtained. Therefore, a marginal closure of the upper portion of the thread does not occur and inflammation around the implant occurs.

In order to solve the above-mentioned problem, in Patent Document 1, there is disclosed an artificial tooth root 100 comprising a columnar insertion portion 101 and a head portion 102 provided on a upper end of the insertion portion 101, wherein at least a part of an outer peripheral surface of the head portion 102 comprises an induction layer 103 having a three-dimensional structure inducing a bone cell and/or an epithelial cell. According to this artificial tooth root 100, by providing the induction layer 103, a gingiva is induced at the upper side of the artificial tooth root 100 so as to cover the artificial tooth root 100, thereby down-growth of the gingiva can be prevented.

PRIOR ART DOCUMENT

Patent Document

Patent Document 1: JP 2010-279653 A

SUMMARY OF THE INVENTION

Problem to be Solved by the Invention

The above-mentioned induction layer 103 can prevent down-growth of the gingiva compared with an artificial tooth root having no induction layer 103. However, in the case of providing the induction layer 103 for inducing the gingiva, the gingiva is hard to grow when substances accelerating breeding of bacteria such as food reaches the induction layer 103. Therefore, in order to prevent down-growth, it is necessary to frequently carry out treatment such as cleaning. The induction layer 103 connects the artificial tooth root to the connective tissue of the bone and the gingiva.

Namely, by inducing the gingiva onto the head portion 102 of the insertion portion 101 with the induction layer 103, down-growth can be prevented and it is possible to make the substances accelerating breeding of bacteria be hard to enter into a pocket generated between the artificial tooth root 100 and the gingiva. However, it is preferable to make the substances accelerating breeding of bacteria be hard to be guided to the induction layer 103 itself. Accordingly, an object of the present invention is to provide an implant structure to which substances accelerating breeding of bacteria are hard to be guided.

Means to Solve the Problem

The implant structure of the present invention comprises: an artificial tooth root comprising an artificial tooth root main body having a distal end portion and a proximal end portion with a thread formed at least on the distal end portion side, and an induction portion for inducing a soft tissue provided on an outer periphery of the proximal end portion of the artificial tooth root main body; and a support base attached to the artificial tooth root and having a covering portion at a proximal end side of the support base covering the whole surface of the proximal end portion side of the induction portion, in which the support base is provided with a step portion along its outer periphery from the covering portion toward a distal end side of the support base.

Further, it is preferable that the step portion is in a tapered shape having a diameter decreasing as it is apart from the proximal end of the support base.

Furthermore, it is preferable that an outer periphery of the covering portion is formed along an outer periphery of the induction portion.

It is also preferable that a tooth crown is fixed to the support base.

Furthermore, it is preferable that the induction portion has a three-dimensional structure intertwining highly biocompatible fibers having a diameter of 5 to 100 μm and having a porosity of 10% to 90%.

Effects of the Invention

According to the implant structure of the present invention, since the step portion catches substances accelerating breeding of bacteria, thereby inhibiting the substances accelerating breeding of bacteria from reaching directly to the induction portion. Therefore, it is easy to inhibit down-growth.

BRIEF DESCRIPTION OF THE DRAWINGS (FIG. 1(a)) A plan view of the whole of the implant structure of the present invention.

Figure 1B:
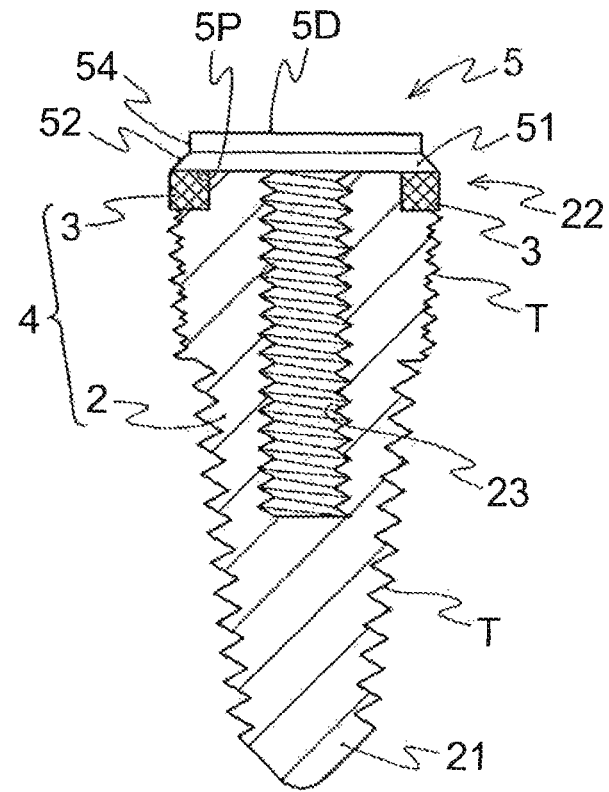

(FIG. 1(b)) A partial cross-sectional view showing a cross-section of the artificial tooth root in the implant structure of the present invention.

(FIG. 2) A cross-sectional view for explaining the support base of the implant structure of the present invention.

(FIG. 3) A partial cross-sectional view showing an implant structure of the present invention further comprising an induction portion on an outer periphery of the artificial tooth root main body.

(FIG. 4) A plan view of an implant structure of the present invention having a tooth crown fixed to the support base.

Figure 5:
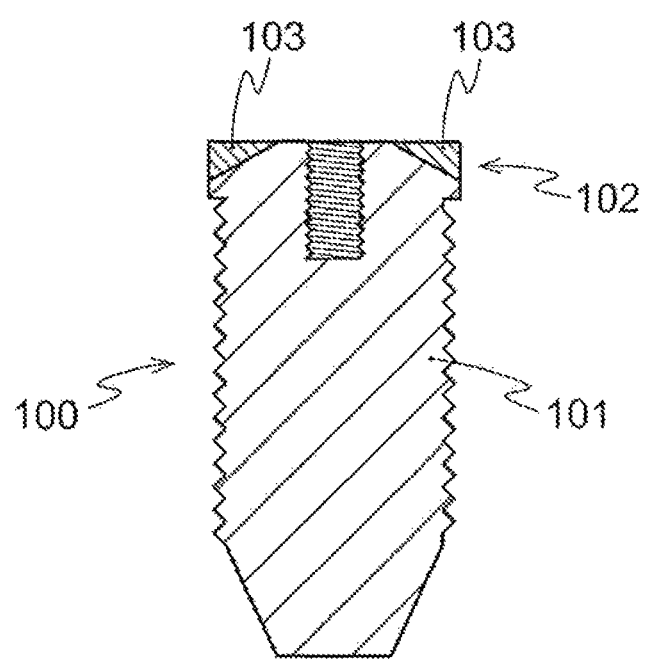

(FIG. 5) A cross-sectional view showing a conventional artificial tooth root.

EMBODIMENT FOR CARRYING OUT THE INVENTION

Referring to the attached drawings, an implant structure of the present invention is explained below in more detail.

As shown in FIG. 1, an implant structure 1 of the present invention comprises an artificial tooth root 4 and a support base 5 attached to the artificial tooth root 4. The artificial tooth root 4 comprises an artificial tooth root main body 2 and an induction portion 3 for inducing a soft tissue. The artificial tooth root main body 2 also comprises a thread T being formed at least on the distal end portion 21 side. The induction portion 3 for inducing a soft tissue is provided on an outer periphery of the proximal end portion 22 of the artificial tooth root main body 2. The support base 5 has a covering portion 51 at a proximal end 5P side of the support base covering the whole surface of the proximal end portion 22 side of the induction portion 3.

The "distal end portion" means an end portion of the artificial tooth root 4 to be inserted into a jawbone, namely, the end portion of the artificial tooth root 4 located at the lower side in FIGS. 1(a) and 1(b). The "proximal end portion" means an end portion to which the support base 5 is attached and which is located opposite to the distal end portion 21 of the artificial tooth root 4. Further, the "proximal end of the support base" means an end portion of the support base where the support base 5 is attached to the artificial tooth root 4 (an end portion located at the lower side of the support base 5 in FIGS. 1(a), 1(b), and 2), and the "distal end of the support base", described below, means an end portion located opposite to the proximal end 5P of the support base 5 (an end portion located at the upper side of the support base 5 in FIGS. 1(a), 1(b), and 2).

The artificial tooth root 4 includes the artificial tooth root main body 2 to be fixed to a hole formed in a jawbone with a thread T, and the induction portion 3 provided on an outer periphery of the proximal end portion 22 of the artificial tooth root main body 2. The induction portion 3 induces a soft tissue (gingiva) after mounting of the artificial tooth root 4 in the jawbone. In the artificial tooth root main body 2, in order to fix the artificial tooth root 4 to the jawbone, the thread T may be formed at least partially on the distal end portion 21 side, or the thread T may be provided on the entire side surface of the artificial tooth root main body 2 from the distal end portion 21 side of the artificial tooth root 4 up to the proximal end portion 22 side. In the artificial tooth root main body 2, an engagement hole 23 with an internal thread is formed, and the engagement hole 23 extends downward along an axis X of the artificial tooth root 4 (See FIG. 1) from the proximal end portion 22 of the artificial tooth root main body 2. An engaging portion 53 of the support base (See FIG. 2), which is a fixing means such as an external thread as described below, is inserted into the engagement hole 23 and fixed. The engaging portion extends from the proximal end 5P of the support base 5. In addition, in the case of the support base 5 having a tooth crown 6 (See FIG. 4), in order to support the tooth crown 6, a shaft (not shown in FIG. 4) provided to the support base 5 is inserted and fixed to the tooth crown 6 in the same manner as of the engaging portion 53 of the support base shown in FIG. 2. The support base 5 may serve as a healing abutment or a healing cap.

While the distal end portion 21 can be formed into a shape and structure used in conventional implant structures, the artificial tooth root can be fixedly connected to the jawbone by setting the angle of the distal end portion 21 to 15°-75° depending on an implant position in the jawbone and the diameter of the artificial tooth root main body 2. Further, the distal end portion 21 may be formed in a sphere shape or a drill shape. Furthermore, a material of the distal end portion 21 is not limited particularly as long as it is highly biocompatible, and for example, titanium, titanium alloy, zirconia or the like which is highly biocompatible can be used.

Further, the artificial tooth root 4 can be formed so that its outer diameter at the proximal end portion 22 side is larger than the outer diameter of the thread T of the artificial tooth root main body 2 (the outer diameter of the thread T at the upper side in FIGS. 1(a) and 1(b)), thereby making it possible to prevent generation of a gap between the artificial tooth root main body 2 and the jawbone all the more and generation of down-growth.

The induction portion 3 is provided on the outer periphery of the artificial tooth root main body 2 at the proximal end portion 22. In order to provide the induction portion 3, the outer diameter of the outer periphery of the artificial tooth root main body 2 at the proximal end portion 22 side of the artificial tooth root 4 in the region where the induction portion 3 is provided is reduced so as to be smaller by the width of the induction portion 3 along a part or the whole of the outer periphery. Namely, the induction portion 3 may be formed into a ring shape so as to surround the whole outer periphery of the proximal end portion 22 of the artificial tooth root 4 as shown in FIGS. 1(a) and 1(b), or may be provided partially along the outer periphery of the proximal end portion 22.

The induction portion 3 is for inducing a soft tissue such as a gingiva, and the structure and material are not limited particularly as long as it can induce the soft tissue. For example, the induction portion 3 having a three-dimensional structure intertwining highly biocompatible fibers having a diameter of 5 to 100 μm and having a porosity of 10 to 90% can be used. In the case where the induction portion 3 has a three-dimensional structure intertwining highly biocompatible fibers having a diameter of 5 to 100 μm and having a porosity of 10 to 90%, a soft tissue such as a gingiva positively enters into gaps between the fibers of the induction portion 3 and is stabilized, thus connecting the artificial tooth root 4 to the soft tissue without gaps.

In addition, a pore size of this induction portion 3 having the three-dimensional structure is 2 to 500 μm, particularly preferably 50 to 200 μm. Examples of the highly biocompatible fibers are a titanium fiber or a titanium alloy fiber which is a fiber of a non-bioabsorbable material, metal fibers, for example, made of stainless steel, gold, platinum or cobalt, a polypropylene fiber, a polyethylene terephthalate fiber and synthetic resin fibers made of polyester and fluorine-containing resin. In addition, fibers of a bioabsorbable material such as polylactic acid, chitin, chitosan, polycaprolactone, polyglycolic acid, starch, collagen or the like may be used. Further, sintered granular metals and highly biocompatible porous ceramics can also be used. Examples of the ceramics are bioabsorbable ceramics such as α-tricalcium phosphate and β-tricalcium phosphate, and non-bioabsorbable ceramics such as hydroxyapatite, alumina, zirconia, carbon, calcium phosphate, glass ceramics, titanium nitride and titanium carbide.

Fibrin, Cytokine factors such as a cell inducing factor and a blood vessel inducing factor and a platelet-derived growth factor which are factors in a blood, may be introduced into the induction portion 3, thereby further accelerating induction of cells. These factors may be extracted from natural products (a patient to be cured or other living organism), or may be generated artificially. In addition, a physiologically active substance or a physiologically active agent which activates bio-cells may be absorbed in the induction portion 3.

Figure 3:
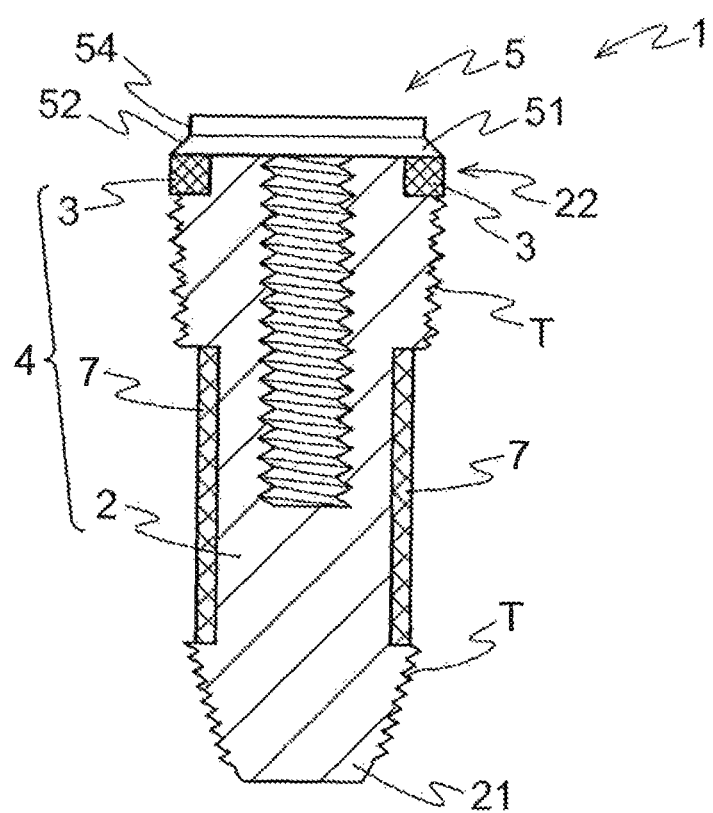
Figure 4:
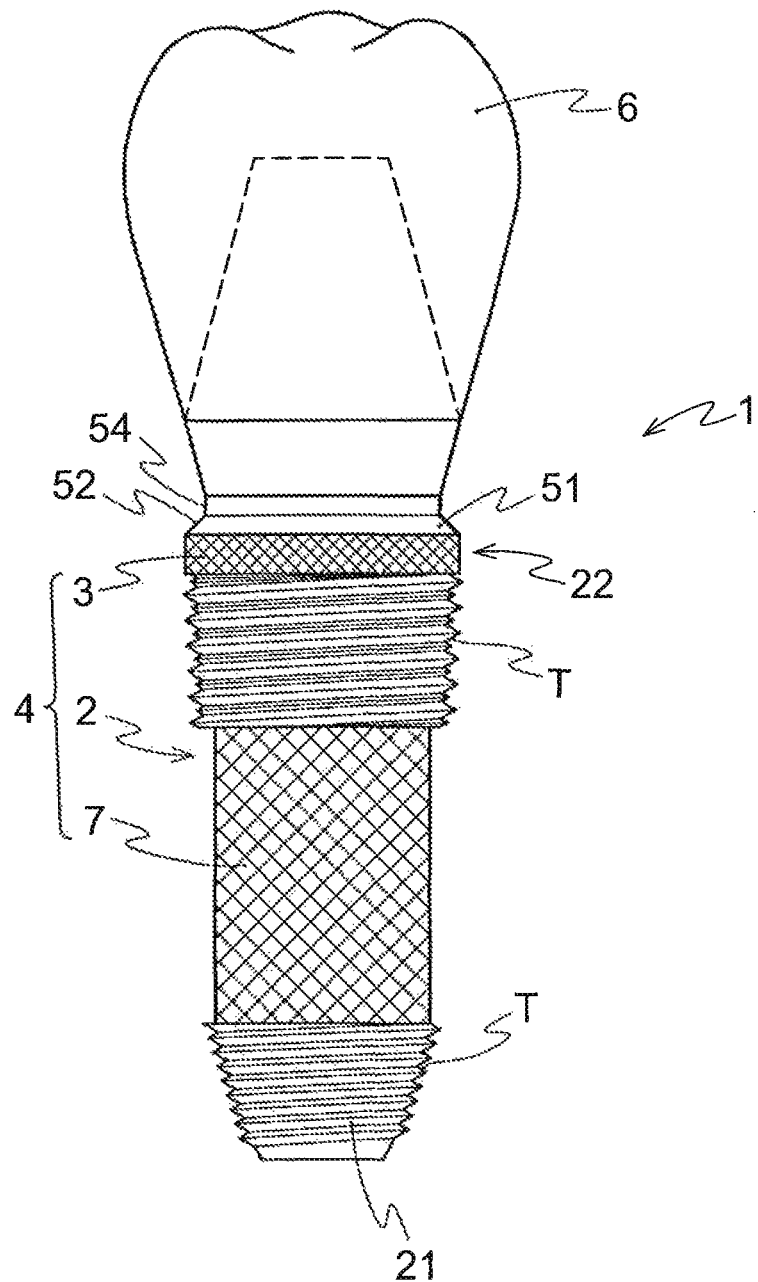

Also, as shown in FIGS. 3 and 4, in order to make it easy to induce bone cells, generate a new bone and intertwine the generated new bone, a bone cell inducing layer 7 for inducing bone cells is provided at an intermediate position between the distal end portion 21. and the proximal end portion 22 of the artificial tooth root 4 so that the artificial tooth root 4 can be fixed to the jawbone more stably.

Figure 2:
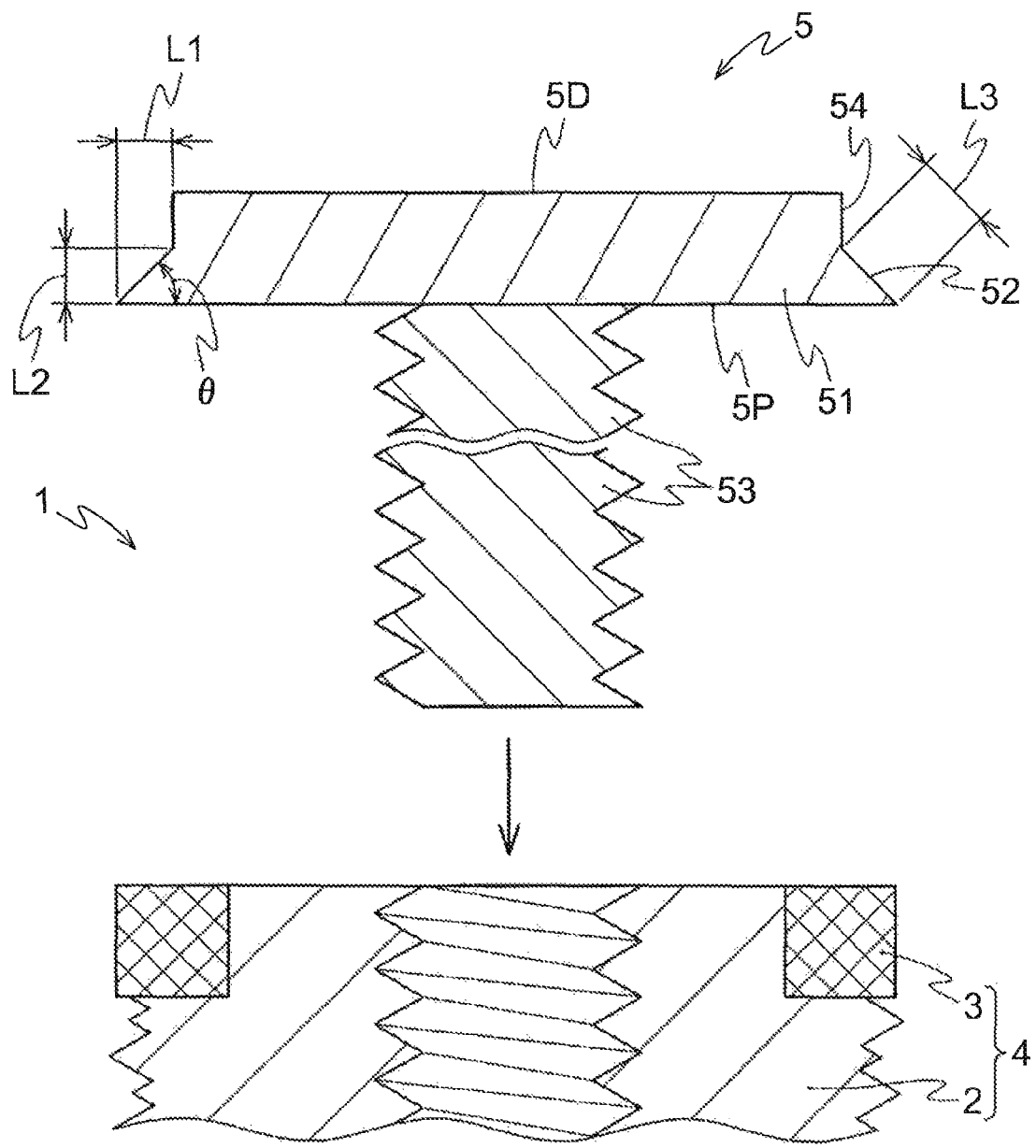

The support base 5 can be used, as shown in FIG. 2, either as a healing cap attached to the artificial tooth root 4 for a given period of time after the operation until a gingiva grows around the artificial tooth root and the artificial root main body 2 and the jawbone are firmly connected each other (See FIG. 2), or as the support base 5 with the tooth crown 6 (See FIG. 4). This support base 5 is provided with the engaging portion 53 of the support base having an external thread for engaging with the engagement hole 23 of the artificial tooth root 4 having an internal thread. In the embodiment shown in FIG. 2, the support base 5 is attached to the artificial tooth root 4 by screwing of the support base 5 to the engagement hole 23 of the artificial tooth root 4. However, it is not limited to this embodiment as shown in FIG. 2 as long as the support base 5 can be firmly attached to the artificial tooth root 4.

Further, in the support base 5 shown in FIGS. 1(a), 1(b) and 2, a substantially cylindrical portion 54 is provided on the upper side of the step portion 52. However, as long as the artificial tooth root can be attached and detached easily, it goes without saying that the support base 5 may be in a substantially conical shape or other shape without providing a substantially cylindrical portion 54 on the upper side of the step portion 52.

Furthermore, a material of the support base 5 is not limited particularly similarly to the artificial tooth root main body 2 as long as it is a highly biocompatible material, and, for example, titanium or titanium alloy having high biocompatibility can be used.

As shown in FIGS. 1(a), 1(b) and 2, the support base 5 to be attached to the artificial tooth root 4 has, at the side of the proximal end 5P of support base, the covering portion 51 covering the whole surface of the induction portion 3 at the proximal end portion 22 side (upper side of the induction portion 3 in FIG. 1). The covering portion 51 is a portion for covering the induction portion 3 from above in FIG. 1. Since the covering portion 51 covers the whole surface of the induction portion 3 at the proximal end portion 22 side (upper side in FIG. 1), substances accelerating breeding of bacteria are prevented from directly reaching the induction portion 3 from the proximal end portion 22 side, thereby making it possible to inhibit contacting of the substances accelerating breeding of bacteria with the induction portion 3 and inhibit breeding of bacteria at the induction portion 3. Therefore, there is no necessity of frequently cleaning of the induction portion 3 to prevent down-growth, and maintenance of the induction portion 3 becomes easy. In addition, the growth of the gingiva at the induction portion 3 can be accelerated. The covering portion 51 is not limited particularly as long as it can cover at least the whole surface of the proximal end portion 22 side of the induction portion 3, and the covering portion 51 may be formed so as to protrude out of the outer periphery of the induction portion 3 and extend outward in the radial direction of the artificial tooth root main body 2.

As shown in FIGS. 1(a) and 1(b), in order to surely cover the induction portion 3, it is preferable that the outer periphery of the covering portion 51 is formed along the outer periphery of the induction portion 3.

As shown in FIG. 1, the support base 5 is provided with a step portion 52 along the outer periphery from the covering portion 51 toward a distal end 5D side of the support base 5 (upper side of the support base 5 in FIG. 1). The step portion 52 is not limited to one shown in FIG. 1 which is in a tapered shape having a diameter decreasing as it is apart from the proximal end portion 22, and the step portion 52 may be in the form of stairs along the direction of the axis X (See FIG. 1(a)) of the artificial tooth root 4. In FIGS. 1(a), 1(b) and 2, while the step portion 52 is formed such that a boundary between the proximal end 5P of the support base 5 and the step portion 52 is formed in an sharp edge, the step portion 52 and a rising portion (not shown) can be formed. The rising portion (not shown) is provided at a given height in the vertical direction (an upward direction in FIG. 2) from the periphery of the proximal end 5P of the support base. The step portion 52 is formed from the upper end of the rising portion. The "step portion" includes one having such a rising portion in the midst of the tapered step portion 52 and one formed by combination of the tapered step portion 52 and the step portion 52 in the form of stairs.

In the step portion 52, a ratio of a length L1 (See FIG. 2) in the radial direction of the step portion 52 to a height L2 (See FIG. 2) of the step portion 52, namely, L1/L2 is not limited particularly. In the case of the tapered step portion 52, an angle θ (See FIG. 2) formed by the proximal end 5P of the support base 5 and the step portion 52 is not limited particularly as long as it is within a range of 0°<θ<90°. In order to trap substances accelerating breeding of bacteria at the step portion 52, 0<L1/L2≤1 is preferred (angle θ (See FIG. 2): 0°<θ≤45°). In addition, in the case of the step portion 52 in the form of stairs, the number of stairs, and the width and height of the stair of the step portion 52 in the form of stairs are not limited particularly.

In the case of the tapered step portion 52, a length L3 of the tapered step portion 52 is not limited particularly, and is preferably within a range of 0.1≤L3≤5.0 (mm) in order to efficiently trap substances accelerating breeding of bacteria at the step portion 52.

Since food remnants and other substances accelerating breeding of bacteria are trapped by the step portion 52 formed on the support base 5 before they reach the induction portion 3, growth of the gingiva at the induction portion 3 can be accelerated and down-growth can be inhibited. Further, since the gingiva growing after implant operation is formed along the step portion 52, a pocket is hard to be formed in the vertical direction between the gingiva and the artificial tooth root 4, and the step portion 52 catches substances accelerating breeding of bacteria to inhibit the substances from directly reaching the induction portion 3, which makes inhibition of down-growth easy. In the embodiments shown in FIGS. 1 to 4, the substantially cylindrical portion 54 is provided, but the substantially cylindrical portion 54 is not necessarily provided. The substantially cylindrical portion 54 may not be provided depending on the length of the step portion 52 and the relationship between the outer diameters of the step portion 52 and the support base 5.

As shown in FIG. 1, the step portion 52 is preferably in a tapered shape having a diameter decreasing as it is apart from the proximal end 5P of the covering portion 51 of the support base. With the tapered step portion 52 having a smooth surface, growth of the gingiva is not interfered, substances accelerating breeding of bacteria are inhibited from directly reaching the induction portion 3, and down-growth can be inhibited.

EXPLANATION OF SYMBOLS

1 Implant structure
2 Artificial tooth root main body
21 Distal end portion
22 Proximal end portion
23 Engagement hole
3 Induction portion
4 Artificial tooth root
5 Support base
51 Covering portion
52 Step portion
53 Engaging portion of support base
54 Substantially cylindrical portion
5D Distal end of support base
5P Proximal end of support base
6 Tooth crown
7 Bone cell inducing layer
T Thread

The invention claimed is:

1. An implant structure comprising:
   an artificial tooth root including an artificial tooth root main body having a distal end portion and a proximal end portion with a thread formed at least on an outer periphery of a distal end portion side of the artificial tooth root main body and on an outer periphery of a proximal end portion side of the artificial tooth root main body, and an induction portion for inducing a soft tissue provided on an outer periphery of the proximal end portion of the artificial tooth root main body; and
   a support base attached to the artificial tooth root and having a covering portion at a proximal end side of the support base covering and facing the whole surface of a proximal end portion side of the induction portion wherein the proximal end side is a side where the support base is attached to the artificial tooth root,
   wherein the induction portion is a three-dimensional structure intertwining highly biocompatible fibers,
   wherein the support base is provided with:
      a step portion along its outer periphery from the covering portion toward a distal end side of the support base wherein the step portion is in a tapered shape having a diameter decreasing with increasing distance from a proximal end of the support base; and
      a substantially cylindrical portion on an upper side of the step portion,
   wherein an angle θ between the proximal end of the support base and a surface of the step portion is within a range of $0° < \theta \leq 45°$, and
   wherein the covering portion, the induction portion and the thread formed on the outer periphery of the proximal end portion side of the artificial tooth root main body are formed in an order of the covering portion, the induction portion and the thread formed on the outer periphery of the proximal end portion side of the artificial tooth root main body in a direction from the support base to the distal end portion.

2. The implant structure of claim 1, wherein an outer periphery of the covering portion is formed along an outer periphery of the induction portion.

3. The implant structure of claim 1, wherein a tooth crown is fixed to the support base.

4. The implant structure of claim 1, wherein highly biocompatible fibers have a diameter of 5 to 100 μm and having a porosity of 10 to 90%.

5. The implant structure of claim 1, wherein the covering portion is exposed in a mouth when the implant structure is mounted in the mouth.

6. The implant structure of claim 1, wherein the implant structure further comprises a bone cell inducing layer on an outer periphery of the artificial tooth root main body between the thread formed on the outer periphery of the distal end portion side of the artificial tooth root main body and the thread formed on the outer periphery of the proximal end portion side of the artificial tooth root main body.

* * * * *